United States Patent
Berger et al.

(10) Patent No.: US 11,912,780 B2
(45) Date of Patent: Feb. 27, 2024

(54) ANTI-CD45-BASED CONDITIONING METHODS AND USES THEREOF IN CONJUNCTION WITH GENE-EDITED CELL-BASED THERAPIES

(71) Applicant: Actinium Pharmaceuticals, Inc., New York, NY (US)

(72) Inventors: Mark Berger, New York, NY (US); Keisha Thomas, Brooklyn, NY (US); Sandesh Seth, New York, NY (US); Dale Lincoln Ludwig, Rockaway, NJ (US)

(73) Assignee: ACTINIUM PHARMACEUTICALS, INC., New York, NY (US)

( * ) Notice: Subject to any disclaimer, the term of this patent is extended or adjusted under 35 U.S.C. 154(b) by 469 days.

(21) Appl. No.: 16/639,911

(22) PCT Filed: Oct. 25, 2018

(86) PCT No.: PCT/US2018/057493
§ 371 (c)(1),
(2) Date: Feb. 18, 2020

(87) PCT Pub. No.: WO2019/084258
PCT Pub. Date: May 2, 2019

(65) Prior Publication Data
US 2020/0255520 A1 Aug. 13, 2020

Related U.S. Application Data

(60) Provisional application No. 62/700,978, filed on Jul. 20, 2018, provisional application No. 62/693,517, filed on Jul. 3, 2018, provisional application No. 62/675,417, filed on May 23, 2018, provisional application No. 62/576,879, filed on Oct. 25, 2017.

(51) Int. Cl.
| | |
|---|---|
| *A61K 51/00* | (2006.01) |
| *A61M 36/14* | (2006.01) |
| *C07K 16/28* | (2006.01) |
| *A61P 37/00* | (2006.01) |
| *A61K 51/10* | (2006.01) |
| *A61P 35/00* | (2006.01) |
| *A61K 35/17* | (2015.01) |
| *A61K 39/00* | (2006.01) |
| *A61K 9/00* | (2006.01) |

(52) U.S. Cl.
CPC ............ *C07K 16/289* (2013.01); *A61K 35/17* (2013.01); *A61K 51/1027* (2013.01); *A61K 51/1096* (2013.01); *A61P 35/00* (2018.01); *A61P 37/00* (2018.01); *A61K 9/0019* (2013.01); *A61K 2039/505* (2013.01)

(58) Field of Classification Search
CPC .. C07K 16/289; A61K 35/17; A61K 51/1027; A61K 51/1096; A61K 9/0019; A61K 2039/505; A61P 35/00; A61P 37/00; C12N 15/90

See application file for complete search history.

(56) References Cited

U.S. PATENT DOCUMENTS

| | | |
|---|---|---|
| 5,273,738 A | 12/1993 | Matthews et al. |
| 2014/0314795 A1 | 10/2014 | Hudecek et al. |
| 2016/0114026 A1 | 4/2016 | Kuzmin et al. |
| 2016/0155728 A1 | 6/2016 | Zhao et al. |
| 2016/0296562 A1 | 10/2016 | Cordoba et al. |
| 2017/0049819 A1 | 3/2017 | Friedman et al. |
| 2017/0080104 A1 | 3/2017 | Irvine et al. |
| 2017/0224737 A1* | 8/2017 | Shizuru .................. A61P 37/06 |
| 2017/0326259 A1 | 11/2017 | Kaushik |
| 2018/0008638 A1 | 1/2018 | Campana et al. |
| 2018/0162939 A1 | 6/2018 | Chen et al. |
| 2019/0013409 A1 | 5/2019 | Li et al. |

FOREIGN PATENT DOCUMENTS

WO WO-2016201047 A1 * 12/2016 ............. A61K 35/28

OTHER PUBLICATIONS

Matthews et al. (Blood 1995, 85, 1122-1131).*
Ali et al. (Blood Reviews 2016, 30, 389-399).*
McKinney-Freeman et al. (PNAS 2002, 99, 1341-1346).*
Ralph et al. (J. Immunol. 1984, 132, 2510-2514).*
Matthews et al. (Blood 1999, 94, 1273-1247).*
FHCRC Protocol 1809 NCT #: NCT00119366 (Sep. 17, 2014).*
Jurcic et al. (ASC Educational Book 2014).*
Zhao et al. (Exp. Cell Res. 2006, 312, 2454-2464).*
Benabdallah et al. (Theranostics 2021, vol. 11, Issue 20, p. 9721-9737).*
Jurcic, et al., Targeted Alpha-Particle Immunotherapy for Acute Myeloid Leukemia, American Society of Clinical Oncology Educational Book, 2014, vol. 34, e126-131.
Pagel, John M. et al., I-anti-CD45 antibody plus busulfan and cyclophosphamide before allogeneic hematopoietic cell transplantation for treatment of acute myeloid leukemia in first remission, Blood Journal, Mar. 1, 2006, vol. 107, No. 5, 2184-2191.
Hay et al., "Kinetics and biomarkers of severe cytokine release syndrome after CD19 chimeric antigen receptor-modified T-cell therapy", Blood. 2017;130(21):2295-2306.

(Continued)

*Primary Examiner* — Michael G. Hartley
*Assistant Examiner* — Melissa J Perreira
(74) *Attorney, Agent, or Firm* — Dentons Cohen & Grigsby P.C.

(57) ABSTRACT

This invention provides a method for depleting a subject's hematopoietic stem cells comprising administering to the subject an effective amount of a radiolabeled anti-CD45 antibody, such as $^{131}$I-BC8 or $^{225}$Ac-BC8. This invention also provides a method for treating a subject afflicted with a non-cancerous disorder treatable via genetically edited cell therapy comprising (i) administering to the subject an amount of a radiolabeled anti-CD45 antibody effective to deplete the subject's hematopoietic stem cells, and (ii) after a suitable time period, performing the therapy on the subject to treat the subject's disorder. Finally, this invention provides articles of manufacture for performing the subject methods.

25 Claims, No Drawings

(56) References Cited

OTHER PUBLICATIONS

Actinium, Iomab-ACT: A Pilot Study of 131-I Apamistamab Followed by CD19-Targeted CAR TCell Therapy for Patients With Relapsed or Refractory B-Cell Acute Lymphoblastic Leukemia or Diffuse Large B-Cell Lymphoma, Clinical Trials, 2020, 9 pgs.
Actinium, Actinium Pharmaceuticals, Inc. Awarded Grant by National Institutes of Health to Study Novel Iomab-ACT Targeted Conditioning with a CD19 Car T-Cell Therapy, PRNewswire Press Release Oct. 21, 2020, 4 pgs.
Actinium, Actinium Announces Initiation of Patient Enrollment in Iomab-ACT Trial for Targeted Conditioning Prior to CD19 Car T-Cell Therapy, RNewswire Press Release Mar. 24, 2021, 4 pgs.
Geyer et al., "Iomab with Adoptive Cellular Therapy (Iomab-ACT): A Pilot Study of 131-I Apamistamab Followed By CD19-Targeted CAR T-Cell Therapy for Patients with Relapsed or Refractory B-Cell Acute Lymphoblastic Leukemia or Diffuse Large B-Cell Lymphoma", Blood, vol. 138, Supplement 1, Nov. 2021, p. 4810; obtained at https://www.sciencedirect.com/science/article/abs/pii/S0006497121067057.
Hay et al., (2017) Chimeric Antigen Receptor (CAR) T cells: Lessons Learned from Targeting of CD19 in B cell malignancies Drugs 77(3) 237-245.
Pagel et al., (2009) Allogeneic hematopoietic cell transplantation after conditioning with 131 I-anti-CD45 antibody plus fludarabine and low-dose total body irradiation for elderly patients with advanced acute myeloid leukemia or high-risk myelodysplastic syndrome Blood 114(27); 5444-5453.
Matthews, et al (1999) Phase I Study of 131 I-Anti-CD45 Antibody Plus Cyclophosphamide and Total Body Irradiation for Advanced Acute Leukemia and Myelodysplastic Syndrome Blood 94(4); 1237-1247.
Scheinberg et al., (2011) Actinium-225 in targeted alpha-particle therapeutic applications Curr Radiopharm 4(4); 306-320.
Burke et al., (2003) Cytoreduction with iodine-131-anti-CD33 antibodies before bone marrow transplant for advanced myeloid leukemias Bone Marrow Transplantation 32; 549-556.
Storb et al., (2016) Nonmyeloablative allogeneic hematopoietic cell transplanatation Haematologica 101(5); 521-530.
Parlak et al., (2016) Bone marrow radiation dosimetry of high dose 1311 treatment in differentiated thyroid carcinoma patients International Journal of Radiation Research 14(2); 99-104.
Gardner et al., (2017) Intent-to-treat leukemia remission by CD19 CART cells of defined formulation and dose in children and young adults Blood 129(25); 3322-3331.
Grosso et al., (2015) Immunotherapy in Acute Myeloid Leukemia Cancer 121; 2689-2704.
Atilla et al., (2017) A Review of Myeloablative vs Reduced Intensity/Non-Myeloablative Regimens in Allogeneic Hematopoietic Stem Cell Transplantations Balkan Med J 34; 1-9.
Kenderian et al., (2017) Chimeric Antigen Receptor T Cells and Hematopoietic Cell Transplantation: How Not to Put the CART Before the Horse Biology of Blood and Marrow Transplantation 23; 235-246.
Irving et al., (2017) Engineering Chimeric Antigen Receptor T-Cells for Racing in Solid Tumors: Don't Forget the Fuel Frontiers in Immunology 8(267); 1-19.
Dudley et al., (2005) Adoptive Cell Transfer Therapy Following Non-Myeloablative but Lymphodepleting Chemotherapy for the Treatment of Patients With Refractory Metastatic Melanoma J Clinic Oneal 23(10); 2346-2357.
Ren et al., Multiplex Genome Editing to Generate Universal CAR T Cells Resistant to PD1 Inhibition, Clin., Cancer Res, (May 1, 2017), 23(9): 2255-2266.
Eom, H. et al., Phase I Clinical Trial of 4-1BB-based Adoptive T-Cell Therapy for Epstein-Barr Virus (EBV)-positive Tumors, Journal of Immunotherapy, 2016, 39(3): 140-148.

\* cited by examiner

ANTI-CD45-BASED CONDITIONING METHODS AND USES THEREOF IN CONJUNCTION WITH GENE-EDITED CELL-BASED THERAPIES

CROSS-REFERENCE TO RELATED APPLICATION

The present application is a 371 national entry of PCT/US2018/057493 filed Oct. 25, 2018, which claims the benefit under 35 U.S.C. § 119(e) of prior U.S. Provisional Application Ser. No. 62/576,879, titled "Methods for Cancer Treatment Using Anti-CD45 Immunoglobin and Adoptive Cell Therapies," filed Oct. 25, 2017; U.S. Provisional Application Ser. No. 62/675,417, titled "Anti-CD45-Based Lymphodepletion Methods and Uses Thereof in Conjunction with Act-Based Cancer Therapies," filed May 23, 2018; U.S. Provisional Application Ser. No. 62/693,517, titled "Anti-CD45-Based Conditioning Methods and Uses Thereof in Conjunction with Gene-Edited Cell-Based Therapies," filed Jul. 3, 2018; and U.S. Provisional Application Ser. No. 62/700,978, titled "Anti-CD45-Based Lymphodepletion Methods and Uses Thereof in Conjunction with Act-Based Cancer Therapies," filed Jul. 20, 2018, the contents of all of which are each incorporated by reference here into this application.

FIELD OF THE INVENTION

The present invention relates to radiolabeled anti-CD45 antibody-based methods for depleting a subject's hematopoietic stem cells. When these methods precede certain gene-edited cell-based therapies, they can safely and effectively enhance the performance of such therapies.

BACKGROUND OF THE INVENTION

Gene editing technologies have advanced substantially with the advent of site-specific editing methods, such as TALEN, CRISPR/cas9, and zinc finger nuclease (ZFN) methods. These methods have therapeutic potential for patients afflicted with non-malignant hereditary diseases such as hemoglobinopathies, congenital immunodeficiencies, and viral-based disorders like AIDS. Gene editing technology makes it feasible to treat and even cure, for example, germline blood disorders such as severe combined immunodeficiency disease (SCID), sickle cell disease (SCD), β-thalassemia and Fanconi's anemia.

Gene editing precisely and permanently alters a sequence of genomic DNA that remains under endogenous genetic regulation and control for proper and appropriate expression of the modified genetic element. There are presently four major classes of nucleases for human genome gene editing: zinc finger nucleases (ZFNs), transcription activator-like effector nucleases (TALENs), meganucleases (MNs), and clustered regularly interspaced short palindromic repeats (CRISPR/Cas9). Each of these can recognize and bind a specific target sequence of DNA. Depending on the properties of the approach, the target DNA can be cleaved on one or both strands. To correct a mutation, a correction template is used for homology-directed repair of the introduced break at the site of the targeted lesion.

It is common to use a combination of highly cytotoxic chemotherapy agents (such as busulfan, cyclophosphamide, melphalan, fludarabine, thiotepa and/or treosulfan) to deplete a patient's hematopoietic stem cells prior to gene-edited stem cell therapy. In addition, total lymphoid radiation may be used. Although these agents reduce stem cell levels, they are highly toxic and result in nonspecific destruction of the immune system and possibly of other normal tissues. Not all patients can tolerate them.

There is an unmet need for a better way to deplete a subject's hematopoietic stem cells prior to gene-edited cell-based therapy.

SUMMARY OF THE INVENTION

This invention provides a method for depleting a subject's hematopoietic stem cells comprising administering to the subject an effective amount of a radiolabeled anti-CD45 antibody.

This invention also provides a method for treating a subject afflicted with a non-cancerous disorder treatable via genetically edited cell therapy comprising (i) administering to the subject an amount of a radiolabeled anti-CD45 antibody effective to deplete the subject's hematopoietic stem cells, and (ii) after a suitable time period, performing the therapy on the subject to treat the subject's disorder.

Finally, this invention provides an article of manufacture comprising (a) a radiolabeled anti-CD45 antibody, and (b) a label instructing the user to administer to a subject an amount of the antibody effective to deplete the subject's hematopoietic stem cells.

DETAILED DESCRIPTION OF THE INVENTION

This invention provides radiolabeled anti-CD45 antibody-based methods for depleting a subject's hematopoietic stem cells, and related methods and articles of manufacture. When these methods precede certain gene-edited cell-based therapies, the methods are able to enhance the outcome of those therapies while minimizing adverse effects.

Throughout this application, various publications are cited. The disclosure of these publications is hereby incorporated by reference into this application to describe more fully the state of the art to which this invention pertains.

Definitions

In this application, certain terms are used which shall have the meanings set forth as follows.

The singular forms "a," "an," "the" and the like include plural referents unless the context clearly dictates otherwise. Thus, for example, reference to "an" antibody includes both a single antibody and a plurality of different antibodies.

The term "about" when used before a numerical designation, e.g., temperature, time, amount, and concentration, including a range, indicates approximations which may vary by ±10%, ±5%, or ±1%.

As used herein, "administer", with respect to an antibody, means to deliver the antibody to a subject's body via any known method suitable for antibody delivery. Specific modes of administration include, without limitation, intravenous, transdermal, subcutaneous, intraperitoneal and intrathecal administration. Exemplary administration methods for antibodies may be as substantially described in International Publication No. WO 2016/187514, incorporated by reference herein.

In addition, in this invention, antibodies can be formulated using one or more routinely used pharmaceutically acceptable carriers. Such carriers are well known to those skilled in the art. For example, injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's).

As used herein, the term "antibody" includes, without limitation, (a) an immunoglobulin molecule comprising two heavy chains and two light chains and which recognizes an antigen; (b) polyclonal and monoclonal immunoglobulin molecules; (c) monovalent and divalent fragments thereof (e.g., di-Fab); and (d) bi-specific forms thereof. Immunoglobulin molecules may derive from any of the commonly known classes, including but not limited to IgA, secretory IgA, IgG and IgM. IgG subclasses are also well known to those in the art and include, but are not limited to, human IgG1, IgG2, IgG3 and IgG4. Antibodies can be both naturally occurring and non-naturally occurring (e.g., IgG-Fc-silent). Furthermore, antibodies include chimeric antibodies, wholly synthetic antibodies, single chain antibodies, and fragments thereof. Antibodies may be human, humanized or nonhuman.

As used herein, an "anti-CD45 antibody" is an antibody that binds to any available epitope of CD45. According to certain aspects, the anti-CD45 antibody binds to the epitope recognized by the monoclonal antibody "BC8." BC8 is known, as are methods of making it. Likewise, methods of labeling BC8 with $^{131}$I are known. These methods are described, for example, in International Publication No. WO 2017/155937.

As used herein, "depleting", with respect to a subject's hematopoietic stem cells ("HSCs", i.e., multipotential hematopoietic stem cells (also referred to as hemocytoblasts)) shall mean to lower the population of the subject's HSCs. According to certain aspects, depleting a subject's HSCs means reducing the subject's HSC population by at least 10%, 20%, 30%, 40%, 50%, 60%, 70%, 80%, 90%, 95% or 99%. According to certain aspects, depleting a subject's HSCs means reducing the subject's HSC population by 100%. Methods for measuring HSC populations are routine. They include, for example, the use of flow cytometry to detect human HSCs in a bone marrow sample, and staining for various cell surface markers (such as Lin, CD34, CD38, CD43, CD45RO, CD45RA, CD59, CD90, CD109, CD117, CD133, CD166, and HLA DR). Reduction of a patient's immune cells may also be detected in peripheral blood. This can be accomplished, for example, by determining absolute lymphocyte counts (ALCs) via detection of CD3-, CD4- and CD8-positive cells as an indication of immune suppression.

As used herein, an amount of a radiolabeled anti-CD45 antibody, when administered, is "effective" if it reduces the subject's HSC level.

According to aspects where the radiolabeled anti-CD45 antibody is $^{131}$I-BC8, the effective amount is below, for example, 1,200 mCi (i.e., where the amount of $^{131}$I-BC8 administered to the subject delivers a total body radiation dose of below 1,200 mCi).

According to aspects where the antibody is $^{131}$I-BC8, the effective amount is below 1,100 mCi, below 1,000 mCi, below 900 mCi, below 800 mCi, below 700 mCi, below 600 mCi, below 500 mCi, below 400 mCi, below 350 mCi, below 300 mCi, below 250 mCi, below 200 mCi, below 150 mCi, below 100 mCi, below 50 mCi, below 40 mCi, below 30 mCi, below 20 mCi or below 10 mCi.

According to aspects where the antibody is $^{131}$I-BC8, the effective amount is from 1 mCi to 10 mCi, from 1 mCi to 200 mCi, from 10 mCi to 20 mCi, from 10 mCi to 30 mCi, from 10 mCi to 40 mCi, from 10 mCi to 50 mCi, from 10 mCi to 100 mCi, from 10 mCi to 150 mCi, from 10 mCi to 200 mCi, from 20 mCi to 30 mCi, from 30 mCi to 40 mCi, from 40 mCi to 50 mCi, from 50 mCi to 100 mCi, from 50 mCi to 150 mCi, from 50 mCi to 200 mCi, from 60 mCi to 140 mCi, from 70 mCi to 130 mCi, from 80 mCi to 120 mCi, from 90 mCi to 110 mCi, from 100 mCi to 150 mCi, from 150 mCi to 200 mCi, from 200 mCi to 250 mCi, from 200 mCi to 300 mCi, from 200 mCi to 350 mCi, from 200 mCi to 400 mCi, from 200 mCi to 500 mCi, from 200 mCi to 600 mCi, from 200 mCi to 700 mCi, from 200 mCi to 800 mCi, from 200 mCi to 900 mCi, from 200 mCi to 1,000 mCi, from 200 mCi to 1,100 mCi, from 200 mCi to 1,200 mCi, from 400 mCi to 500 mCi, from 400 mCi to 600 mCi, from 400 mCi to 700 mCi, from 400 mCi to 800 mCi, from 400 mCi to 900 mCi, from 400 mCi to 1,000 mCi, from 400 mCi to 1,100 mCi, or from 400 mCi to 1,200 mCi.

According to aspects where the antibody is $^{131}$I-BC8, the effective amount is 1 mCi, 10 mCi, 20 mCi, 30 mCi, 40 mCi, 50 mCi, 60 mCi, 70 mCi, 80 mCi, 90 mCi, 100 mCi, 110 mCi, 120 mCi, 130 mCi, 140 mCi, 150 mCi, 200 mCi, 250 mCi, 300 mCi, 350 mCi, 400 mCi, 450 mCi, 500 mCi, 550 mCi, 600 mCi, 650 mCi, 700 mCi, 750 mCi, 800 mCi, 850 mCi, 900 mCi, 950 mCi, 1,000 mCi, 1,050 mCi, 1,100 mCi, 1,150 mCi, or 1,200 mCi.

For an antibody labeled with a radioisotope, the majority of the drug administered to a subject typically consists of non-labeled antibody, with the minority being the labeled antibody. The ratio of labeled to non-labeled antibody can be adjusted using known methods. Thus, accordingly to certain aspects of the present invention, the anti-CD45 antibody may be provided in a total protein amount of up to 60 mg, such as 5 mg to 45 mg, or a total protein amount of between 0.1 mg/kg patient weight to 1.0 mg/kg patient weight, such as 0.2 mg/kg patient weight to 0.6 mg/kg patient weight.

According to certain aspects of the present invention, the radiolabeled anti-CD45 antibody may comprise a labeled fraction and an unlabeled fraction, wherein the ratio of labeled:unlabeled may be from about 0.01:10 to 1:1, such as 0.1:10 to 1:1 labeled:unlabeled. Moreover, the radiolabeled anti-CD45 antibody may be provided as a single dose composition tailored to a specific patient, wherein the amount of labeled and unlabeled anti-CD45 antibody in the composition may depend on at least a patient weight, age, and/or disease state or health status.

According to aspects where the radiolabeled anti-CD45 antibody is $^{225}$Ac-BC8, the effective amount is below, for example, 5.0 µCi/kg (i.e., where the amount of $^{225}$Ac-BC8 administered to the subject delivers a radiation dose of below 5.0 µCi per kilogram of subject's body weight).

According to aspects where the antibody is $^{225}$Ac-BC8, the effective amount is below 4.5 µCi/kg, 4.0 µCi/kg, 3.5 µCi/kg, 3.0 µCi/kg, 2.5 µCi/kg, 2.0 µCi/kg, 1.5 µCi/kg, 1.0 µCi/kg, 0.9 µCi/kg, 0.8 µCi/kg, 0.7 µCi/kg, 0.6 µCi/kg, 0.5 µCi/kg, 0.4 µCi/kg, 0.3 µCi/kg, 0.2 µCi/kg, 0.1 µCi/kg or 0.05 µCi/kg.

According to aspects where the antibody is $^{225}$Ac-BC8, the effective amount is from 0.05 µCi/kg to 0.1 µCi/kg, from 0.1 µCi/kg to 0.2 µCi/kg, from 0.2 µCi/kg to 0.3 µCi/kg, from 0.3 µCi/kg to 0.4 µCi/kg, from 0.4 µCi/kg to 0.5 µCi/kg, from 0.5 µCi/kg to 0.6 µCi/kg, from 0.6 µCi/kg to 0.7 µCi/kg, from 0.7 µCi/kg to 0.8 µCi/kg, from 0.8 µCi/kg to 0.9 µCi/kg, from 0.9 µCi/kg to 1.0 µCi/kg, from 1.0 µCi/kg to 1.5 µCi/kg, from 1.5 µCi/kg to 2.0 µCi/kg, from 2.0 µCi/kg to 2.5 µCi/kg, from 2.5 µCi/kg to 3.0 µCi/kg, from 3.0 µCi/kg to 3.5 µCi/kg, from 3.5 µCi/kg to 4.0 µCi/kg, from 4.0 µCi/kg to 4.5 µCi/kg, or from 4.5 µCi/kg to 5.0 µCi/kg.

According to aspects where the antibody is $^{225}$Ac-BC8, the effective amount is 0.05 µCi/kg, 0.1 µCi/kg, 0.2 µCi/kg, 0.3 µCi/kg, 0.4 µCi/kg, 0.5 µCi/kg, 0.6 µCi/kg, 0.7 µCi/kg, 0.8 µCi/kg, 0.9 µCi/kg, 1.0 µCi/kg, 1.5 µCi/kg, 2.0 µCi/kg, 2.5 µCi/kg, 3.0 µCi/kg, 3.5 µCi/kg, 4.0 µCi/kg or 4.5 µCi/kg.

As used herein, "non-cancerous disorders" include, without limitation, hemoglobinopathies (e.g., SCD and β-thalassemia), congenital immunodeficiencies (e.g., SCID and Fanconi's anemia) and viral infections (e.g., an HIV infection). Non-cancerous disorders exclude, for example, solid cancers (e.g., tumors) and hematologic malignancies.

As used herein, the term "subject" includes, without limitation, a mammal such as a human, a non-human primate, a dog, a cat, a horse, a sheep, a goat, a cow, a rabbit, a pig, a rat and a mouse. Where the subject is human, the subject can be of any age. According to certain aspects, the subject is an infant. According to further aspects, the subject is one, two, three, four, five, six, seven, eight, nine or 10. According to yet further aspects, the subject is from 10 to 15, or from 15 to 20. According to yet further aspects, the subject is 20 or older, 25 or older, 30 or older, 35 or older, 40 or older, 45 or older, 50 or older, 55 or older, 60 or older, 65 or older, 70 or older, 75 or older, 80 or older, 85 or older, or 90 or older.

As used herein, a "suitable time period" after administering a radiolabeled anti-CD45 antibody to a subject and before performing therapy on the subject is a time period sufficient to permit the administered antibody to deplete the subject's HSCs and/or for the subject's HSCs to remain depleted. According to certain aspects, the suitable time period is fewer than 15 days, fewer than 14 days, fewer than 13 days, fewer than 12 days, fewer than 11 days, fewer than 10 days, fewer than 9 days, fewer than 8 days, fewer than 7 days, fewer than 6 days, fewer than 5 days, fewer than 4 days, or fewer than 3 days. According to certain aspects, the suitable time period is 1 day, 2 days, 3 days, 4 days, 5 days, 6 days, 7 days, 8 days, 9 days, 10 days, 11 days, 12 days, 13 days, 14 days, 15 days, or more than 15 days.

As used herein, a "radioisotope" can be an alpha-emitting isotope, a beta-emitting isotope, and/or a gamma-emitting isotope. Examples of radioisotopes include the following: $^{131}$I, $^{125}$I, $^{123}$I, $^{90}$Y, $^{177}$Lu, $^{186}$Re, $^{188}$Re, $^{89}$Sr, $^{153}$Sm, $^{32}$P, $^{225}$Ac, $^{213}$Bi, $^{213}$Po, $^{211}$At, $^{212}$Bi, $^{213}$Bi, $^{223}$Ra, $^{227}$Th, $^{149}$Tb, $^{137}$Cs, $^{212}$Pb an $^{103}$Pd. Thus, the radiolabeled antibodies envisioned in this invention include, without limitation, $^{131}$I-BC8, $^{125}$I-BC8, $^{123}$I-BC8, $^{90}$Y-BC8, $^{177}$Lu-BC8, $^{186}$Re-BC8, $^{188}$Re-BC8, $^{89}$Sr-BC8, $^{153}$Sm-BC8, $^{32}$P-BC8, $^{225}$Ac-BC8, $^{213}$Bi-BC8, $^{213}$Po-BC8, $^{211}$At-BC8, $^{212}$Bi-BC8, $^{213}$Bi-BC8, $^{223}$Ra-BC8, $^{227}$Th-BC8, $^{149}$Tb-BC8, $^{137}$Cs-BC8, $^{212}$Pb-BC8 and $^{103}$Pd-BC8. Methods for affixing a radioisotope to an antibody (i.e., "labeling" an antibody with a radioisotope) are well known.

As used herein, "treating" a subject afflicted with a disorder shall include, without limitation, (i) slowing, stopping or reversing the disorder's progression, (ii) slowing, stopping or reversing the progression of the disorder's symptoms, (iii) reducing, and ideally eliminating, the likelihood of the disorder's recurrence, and/or (iv) reducing, and ideally eliminating, the likelihood that the disorder's symptoms will recur. According to certain preferred aspects, treating a subject afflicted with a disorder means (i) reversing the disorder's progression, ideally to the point of eliminating the disorder, and/or (ii) reversing the progression of the disorder's symptoms, ideally to the point of eliminating the symptoms, and/or (iii) reducing or eliminating the likelihood of relapse. Ideally, treating a subject afflicted with a disorder means curing the disorder by removing or otherwise disabling its genetic cause.

Throughout this application, various publications are cited. The disclosure of these publications is hereby incorporated by reference into this application to describe more fully the state of the art to which this invention pertains. Unless otherwise defined, all technical and scientific terms used herein have the same meaning as commonly understood by one of ordinary skill in the art to which the present invention belongs. Although methods and materials similar or equivalent to those described herein can be used in the practice or testing described herein, suitable methods and materials are described below.

Aspects of the Invention

This invention solves an unmet need in the art by providing an unexpectedly superior way to deplete a subject's hematopoietic stem cells, ideally prior to a gene-edited cell-based therapy like genetically edited β-globin hematopoietic stem cell therapy for SCD. This invention employs a radiolabeled anti-CD45 antibody such as $^{131}$I-BC8 for this purpose. The antibody can safely and effectively deplete the subject's hematopoietic stem cells via targeted conditioning. This approach avoids certain adverse effects caused by less specific agents like chemotherapeutics or external beam radiation.

Specifically, this invention provides a method for depleting a subject's hematopoietic stem cells comprising administering to the subject an effective amount of a radiolabeled anti-CD45 antibody. Preferably, the subject is human.

This depletion method (also referred to herein as a conditioning method) is useful, for example, for improving the outcome of a subsequent gene-edited cell-based therapy where the depletion of hematopoietic stem cells is desirable. According to certain preferred aspects of this method, the subject is afflicted with a non-cancerous disorder treatable via genetically edited cell therapy and is about to undergo such therapy to treat the disorder.

Examples of non-cancerous disorders include, without limitation, hemoglobinopathies (e.g., SCD and β-thalassemia), congenital immunodeficiencies (e.g., SCID and Fanconi's anemia) and viral infections (e.g., HIV infection). According to certain aspects, the disorder is SCD and the therapy is genetically edited β-globin hematopoietic stem cell therapy. The stem cell therapy can be allogenic or autologous, for example. According to certain aspects, the disorder is SCID and the therapy is genetically edited hematopoietic stem cell therapy, wherein the edited gene is the common gamma chain (γc) gene, the adenosine deaminase (ADA) gene and/or the Janus kinase 3 (JAK3) gene. The stem cell therapy can be allogenic or autologous, for example.

According to certain preferred aspects of the subject method, the radiolabeled anti-CD45 antibody is radiolabeled BC8, such as $^{131}$I-BC8 or $^{225}$Ac-BC8. When the radiolabeled BC8 is $^{131}$I-BC8, the effective amount can be, for example, from 10 mCi to 200 mCi, from 200 mCi to 400 mCi, or from 400 mCi to 1,200 mCi. When the radiolabeled BC8 is $^{225}$Ac-BC8, the effective amount can be, for example, from 0.1 µCi/kg to 1.0 µCi/kg, from 1.0 µCi/kg to 3.0 µCi/kg, from 3.0 µCi/kg to 5.0 µCi/kg, or from 0.1 µCi/kg to 5.0 µCi/kg.

This invention also provides a method for treating a subject afflicted with a non-cancerous disorder treatable via genetically edited cell therapy comprising (i) administering to the subject an amount of a radiolabeled anti-CD45 antibody effective to deplete the subject's hematopoietic stem cells, and (ii) after a suitable time period, performing the therapy on the subject to treat the subject's disorder. Preferably, the subject is human.

Examples of non-cancerous disorders include, without limitation, hemoglobinopathies (e.g., SCD and β-thalassemia), congenital immunodeficiencies (e.g., SCID and Fanconi's anemia) and viral infections (e.g., HIV infection). According to certain aspects, the disorder is SCD and the therapy is genetically edited β-globin hematopoietic stem cell therapy. The stem cell therapy can be allogenic or autologous, for example. According to certain aspects, the disorder is SCID and the therapy is genetically edited hematopoietic stem cell therapy, wherein the edited gene is the common gamma chain (γc) gene, the ADA gene and/or the JAK3 gene. The stem cell therapy can be allogenic or autologous, for example.

According to certain preferred aspects of the subject treatment method, the radiolabeled anti-CD45 antibody is radiolabeled BC8, such as $^{131}$I-BC8 or $^{225}$Ac-BC8. When the radiolabeled BC8 is $^{131}$I-BC8, the effective amount can be, for example, from 10 mCi to 200 mCi, from 200 mCi to 400 mCi, or from 400 mCi to 1,200 mCi. When the radiolabeled BC8 is $^{225}$Ac-BC8, the effective amount can be, for example, from 0.1 µCi/kg to 1.0 µCi/kg, from 1.0 µCi/kg to 3.0 µCi/kg, from 3.0 µCi/kg to 5.0 µCi/kg, or from 0.1 µCi/kg to 5.0 µCi/kg. Moreover, the suitable time period between steps (i) and (ii) of this method is preferably from six (6) to 14 days.

This invention provides, among other things, seven specific aspects of the subject method for treating a human subject afflicted with a non-cancerous disorder treatable via genetically edited allogenic or autologous cell therapy. The first comprises (i) administering to the subject from 10 mCi to 200 mCi of $^{131}$I-BC8, and (ii) after 6, 7 or 8 days, performing the therapy on the subject to treat the subject's disorder. The second comprises (i) administering to the subject from 200 mCi to 400 mCi of $^{131}$I-BC8, and (ii) after 8, 9, 10, 11 or 12 days, performing the therapy on the subject to treat the subject's disorder. The third comprises (i) administering to the subject from 400 mCi to 1,200 mCi of $^{131}$I-BC8, and (ii) after 10, 11, 12, 13 or 14 days, performing the therapy on the subject to treat the subject's disorder. The fourth comprises (i) administering to the subject from 0.1 µCi/kg to 5.0 µCi/kg of $^{225}$Ac-BC8, and (ii) after 6, 7 or 8 days, performing the therapy on the subject to treat the subject's disorder. The fifth comprises (i) administering to the subject from 0.1 µCi/kg to 1.0 µCi/kg of $^{225}$Ac-BC8, and (ii) after 6, 7 or 8 days, performing the therapy on the subject to treat the subject's disorder. The sixth comprises (i) administering to the subject from 1.0 µCi/kg to 3.0 µCi/kg of $^{225}$Ac-BC8, and (ii) after 6, 7 or 8 days, performing the therapy on the subject to treat the subject's disorder. The seventh comprises (i) administering to the subject from 3.0 µCi/kg to 5.0 µCi/kg of $^{225}$Ac-BC8, and (ii) after 6, 7 or 8 days, performing the therapy on the subject to treat the subject's disorder.

This invention further provides an article of manufacture comprising (a) a radiolabeled anti-CD45 antibody, and (b) a label instructing the user to administer to a subject an amount of the antibody effective to deplete the subject's hematopoietic stem cells. Preferably, the subject is human.

According to certain preferred aspects of the subject article, the radiolabeled anti-CD45 antibody is radiolabeled BC8, such as $^{131}$I-BC8 or $^{225}$Ac-BC8. When the radiolabeled BC8 is $^{131}$I-BC8, the effective amount can be, for example, from 10 mCi to 200 mCi, from 200 mCi to 400 mCi, or from 400 mCi to 1,200 mCi. When the radiolabeled BC8 is $^{225}$Ac-BC8, the effective amount can be, for example, from 0.1 µCi/kg to 5.0 µCi/kg.

This invention provides, among other things, seven specific aspects of the subject article. The first comprises (a)$^{131}$I-BC8, and (b) a label instructing the user to administer to a human subject from 10 mCi to 200 mCi of the $^{131}$I-BC8. The second comprises (a)$^{131}$I-BC8, and (b) a label instructing the user to administer to a human subject from 200 mCi to 400 mCi of the $^{131}$I-BC8. The third comprises (a)$^{131}$I-BC8, and (b) a label instructing the user to administer to a human subject from 400 mCi to 1,200 mCi of the $^{131}$I-BC8. The fourth comprises (a)$^{225}$Ac-BC8, and (b) a label instructing the user to administer to a human subject from 0.1 µCi/kg to 5.0 µCi/kg of the $^{225}$Ac-BC8. The fifth comprises (a)$^{225}$Ac-BC8, and (b) a label instructing the user to administer to a human subject from 0.1 µCi/kg to 1.0 µCi/kg of the $^{225}$Ac-BC8. The sixth comprises (a)$^{225}$Ac-BC8, and (b) a label instructing the user to administer to a human subject from 1.0 µCi/kg to 3.0 µCi/kg of the $^{225}$Ac-BC8. The seventh comprises (a)$^{225}$Ac-BC8, and (b) a label instructing the user to administer to a human subject from 3.0 µCi/kg to 5.0 µCi/kg of the $^{225}$Ac-BC8.

This invention will be better understood by reference to the examples which follow, but those skilled in the art will readily appreciate that the specific examples detailed are only illustrative of the invention as described more fully in the claims which follow thereafter.

The following aspects are disclosed in this application:

Aspect 1. A method for depleting a subject's hematopoietic stem cells comprising administering to the subject an effective amount of a radiolabeled anti-CD45 antibody.

Aspect 2. The method of aspect 1, wherein the subject is afflicted with a non-cancerous disorder treatable via genetically edited cell therapy and is about to undergo such therapy to treat the disorder, and the effective amount of the radiolabeled anti-CD45 antibody is administered as a single dose.

Aspect 3. The method of aspect 2, wherein the disorder is selected from the group consisting of a hemoglobinopathy, a congenital immunodeficiency, and a viral infection.

Aspect 4. The method of aspect 2, wherein the disorder is selected from the group consisting of sickle cell disease (SCD), severe combined immunodeficiency disease (SCID), 0-thalassemia and Fanconi's anemia.

Aspect 5. The method of aspect 2, wherein the disorder is SCD and the therapy is genetically edited β-globin hematopoietic stem cell therapy.

Aspect 6. The method of aspect 2, wherein the disorder is SCID and the therapy is genetically edited hematopoietic stem cell therapy, wherein the edited gene is selected from the group consisting of the common gamma chain (γc) gene, the adenosine deaminase (ADA) gene and the Janus kinase 3 (JAK3) gene.

Aspect 7. The method according to any one of aspects 1 to 6, wherein the radiolabeled anti-CD45 antibody is radiolabeled BC8.

Aspect 8. The method according to any one of aspects 1 to 7, wherein the radiolabeled anti-CD45 antibody comprises $^{131}$I, $^{125}$I, $^{123}$I, $^{90}$Y, $^{177}$Lu, $^{186}$Re, $^{188}$Re, $^{89}$Sr, $^{153}$Sm, $^{32}$P, $^{225}$Ac, $^{213}$Bi, $^{213}$Po, $^{211}$At, $^{212}$Bi, $^{213}$Bi, $^{223}$Ra, $^{227}$Th, $^{149}$Tb, $^{137}$Cs, $^{212}$Pb and $^{103}$Pd.

Aspect 9. The method according to aspects 7 or 8, wherein the radiolabeled BC8 is $^{131}$I-BC8, and the effective amount of $^{131}$I-BC8 is from 10 mCi to 200 mCi, or from 200 mCi to 400 mCi, or from 400 mCi to 1,200 mCi.

Aspect 10. The method according to aspects 7 or 8, wherein the radiolabeled BC8 is $^{225}$Ac-BC8, and the effective amount of $^{225}$Ac-BC8 is from 0.1 µCi/kg to 5.0 µCi/kg subject weight, or from 0.1 µCi/kg to 1.0 µCi/kg subject weight, or from 1.0 µCi/kg to 3.0 µCi/kg subject weight, or from 3.0 µCi/kg to 5.0 µCi/kg subject weight.

Aspect 11. A method for treating a subject afflicted with a non-cancerous disorder treatable via genetically edited cell therapy comprising (i) administering to the subject an amount of a radiolabeled anti-CD45 antibody effective to deplete the subject's hematopoietic stem cells, and (ii) after a suitable time period, performing the therapy on the subject to treat the subject's disorder.

Aspect 12. The method of aspect 11, wherein the subject is afflicted with a non-cancerous disorder treatable via genetically edited cell therapy and is about to undergo such therapy to treat the disorder, and the effective amount of the radiolabeled anti-CD45 antibody is administered as a single dose.

Aspect 13. The method of aspect 12, wherein the disorder is selected from the group consisting of a hemoglobinopathy, a congenital immunodeficiency, and a viral infection.

Aspect 14. The method of aspect 12, wherein the disorder is selected from the group consisting of sickle cell disease (SCD), severe combined immunodeficiency disease (SCID), 0-thalassemia and Fanconi's anemia.

Aspect 15. The method of aspect 12, wherein the disorder is SCD and the therapy is genetically edited β-globin hematopoietic stem cell therapy.

Aspect 16. The method of aspect 12, wherein the disorder is SCID and the therapy is genetically edited hematopoietic stem cell therapy, wherein the edited gene is selected from the group consisting of the common gamma chain (γc) gene, the adenosine deaminase (ADA) gene and the Janus kinase 3 (JAK3) gene.

Aspect 17. The method of aspect 15 or 16, wherein the stem cell therapy is allogeneic stem cell therapy.

Aspect 18. The method of aspect 15 or 16, wherein the stem cell therapy is autologous stem cell therapy.

Aspect 19. The method according to any one of aspects 11 to 19, wherein the radiolabeled anti-CD45 antibody is radiolabeled BC8, comprising $^{131}$I, $^{125}$I, $^{123}$I, $^{90}$Y, $^{177}$Lu, $^{186}$Re, $^{188}$Re, $^{89}$Sr, $^{153}$Sm, $^{32}$P, $^{225}$Ac, $^{213}$Bi, $^{213}$Po, $^{211}$At, $^{212}$Bi, $^{213}$Bi, $^{223}$Ra, $^{227}$Th, $^{149}$Tb, $^{137}$Cs, $^{212}$Pb and $^{103}$Pd.

Aspect 20. The method according to aspect 19, wherein the radiolabeled BC8 is $^{131}$I-BC8, and the effective amount of $^{131}$I-BC8 is from 10 mCi to 200 mCi administered 6, 7, or 8 days after performing the therapy on the subject to treat the subject's disorder.

Aspect 21. The method according to aspect 19, wherein the radiolabeled BC8 is $^{131}$I-BC8, and the effective amount of $^{131}$I-BC8 is from 200 mCi to 400 mCi administered 8, 9, 10, 11, or 12 days after performing the therapy on the subject to treat the subject's disorder.

Aspect 22. The method according to aspect 19, wherein the radiolabeled BC8 is $^{131}$I-BC8, and the effective amount of $^{131}$I-BC8 is from 400 mCi to 1,200 mCi of $^{131}$I-BC8 administered 10, 11, 12, 13, or 14 days after performing the therapy on the subject to treat the subject's disorder.

Aspect 23. The method according to aspect 19, wherein the radiolabeled BC8 is $^{225}$Ac-BC8, and the effective amount of $^{225}$Ac-BC8 is from 0.1 µCi/kg to 5.0 µCi/kg subject weight administered 6, 7, 8, 9, 10, 11, or 12 days after performing the therapy on the subject to treat the subject's disorder.

Aspect 24. An article of manufacture comprising (a) a radiolabeled anti-CD45 antibody, and (b) a label instructing the user to administer to a subject an amount of the antibody effective to deplete the subject's hematopoietic stem cells.

Aspect 25. The article of aspect 24, wherein the radiolabeled BC8 is $^{131}$I-BC8, and the effective amount of $^{131}$I-BC8 is from 10 mCi to 200 mCi, or from 200 mCi to 400 mCi, or from 400 mCi to 1,200 mCi.

Aspect 26. The article of aspect 24, wherein the radiolabeled BC8 is $^{225}$Ac-BC8, and the effective amount of $^{225}$Ac-BC8 is from 0.1 µCi/kg to 5.0 µCi/kg, or from 0.1 µCi/kg to 1.0 µCi/kg subject weight, or from 1.0 µCi/kg to 3.0 µCi/kg subject weight, or from 3.0 µCi/kg to 5.0 µCi/kg subject weight.

EXAMPLES

Example 1—$^{131}$I-BC8 (Iomab-B)

The Iomab-B drug product is a radio-iodinated anti-CD45 murine monoclonal antibody (mAb) ($^{131}$I-BC8). It is specific for the hematopoietic CD45 antigen. The Iomab-B drug product is supplied as a sterile formulation contained in a container closure system consisting of depyrogenated Type 1 50 mL glass vial, sterilized grey chlorobutyl rubber stopper, and open top style aluminum seal. Each dose vial also contains a drug product fill volume of 45 mL in a 50 mL vial. Similarly, it is provided as a single use dose for complete infusion during intravenous administration, and contains patient-specific radioactivity from 1 mCi to 200 mCi (e.g., 100 mCi or 150 mCi) of $^{131}$I and 6.66-45 mg of BC8. BC8 antibody dose is determined according to the ideal body weight at a level of 0.5 mg/kg. The drug product is co-administered in line with 0.9% Sodium Chloride Injection USP (normal saline solution) to the patients at a ratio of 1:9 of drug product to saline solution. The total drug product and saline infusion volume of approximately 430-450 mL is administered over varied durations, since the infusion rate depends on the amount of BC8 antibody in the 45 mL drug product fill volume.

International Publication No. WO 2017/155937 teaches the full structure of BC8, and methods for making $^{131}$I-BC8.

Example 2—$^{225}$Ac-BC8

Conjugation of BC8 with DOTA and Subsequent Labeling with $^{225}$Ac

The antibody BC8 (2 mg) was equilibrated with conjugation buffer (Na carbonate buffer with 1 mM EDTA, pH=8.5-9.0) by four ultrafiltration spins using a Centricon filter with a MW cutoff of 50,000, or a Vivaspin ultrafiltration tube with a MW cutoff of 50,000. 1.5 ml of conjugation buffer per spin was used. For each spin, the antibody was spun for 5-20 minutes, at 53,000 RPM and at 4° C. to a residual retentate volume of 100-200 µl. The antibody was incubated at 4° C. for 30 minutes following the $2^{nd}$ and $3^{rd}$ spins to allow for equilibration. For DOTA conjugation, a solution of DOTA-pSCN (MW=678) at 3 mg/ml in 0.15M NH40Ac was prepared by dissolution and vortexing. DOTA-pSCN and BC8 antibody (at >5 mg/ml) was mixed together at a 7.5 molar ratio (DOTA:antibody) in an Eppendorf tube and incubated for 15 hours at room temperature. For purification of the DOTA-antibody conjugate, unreacted DOTA-pSCN was removed by seven rounds of ultrafiltration with 1.5 ml of 0.15M NH40Ac buffer, pH=6.5 to a volume of approximately 100 µl. After the final wash, 0.15 M NH40Ac buffer was added to bring the material to a final concentration of approximately 1 mg/ml. The final concentration of the DOTA-BC8 conjugate was measured and the number of DOTA molecules conjugated to the antibody was determined to be 1.2-1.5 DOTA to antibody.

Radiolabeling of DOTA-Antibody Conjugates with $^{225}$Ac

To label the DOTA-BC8 conjugate with $^{225}$Ac, 15 μL 0.15M NH40Ac buffer, pH=6.5, was mixed with 2 μL (10 μg) DOTA-BC8 (5 mg/ml) in an Eppendorf reaction tube. Four μL of 225Ac (10 μCi) in 0.05 M HCl were subsequently added, the contents of the tube were mixed with a pipette tip, and the reaction mixture was incubated at 37° C. for 90 minutes with shaking at 100 rpm. At the end of the incubation period, 3 μL of 1 mM DTPA solution was added to the reaction mixture and incubated at room temperature for 20 minutes to bind un-complexed $^{225}$Ac. Instant thin layer chromatography (ITLC) was performed with a 10 cm silica gel strip and a 10 mM EDTA/normal saline mobile phase to determine the radiochemical purity of $^{225}$Ac-BC8, separating $^{225}$Ac-labeled BC8 from $^{225}$Ac-DTPA and counting sections in a gamma counter equipped with a multichannel analyzer. The radiolabeling efficiency over several runs was determined to be greater than 80%.

Example 3—SCD

This example describes HSC ablation (i.e., 100% depletion) preceding transplant with gene-edited HSCs in patients with SCD.

SCD is the most common hemoglobinopathy worldwide. The incidence of SCD among African Americans is approximately 1 in 500. It is estimated that 100,000 individuals are afflicted in the United States.

SCD is caused by a single nucleotide mutation in the β-globin gene that produces sickle hemoglobin. SCD patients may exhibit anemia, vaso-occlusive crises (VOCs), hemolysis, chronic organ dysfunction, and early mortality. The mortality rate among children with SCD is 0.5 per 100,000. However, the mortality rate in adults is more than 2.5 per 100,000, and median life expectancy is less than 50 years of age for both men and women with SCD.

Currently, the only curative treatment for SCD is a hematopoietic stem cell transplant (HSCT). Unfortunately, HSCTs for SCD are not without problems. According to the Center for International Blood and Marrow Transplant Research, only 1,089 patients with SCD underwent HSCTs from 1991 to April 2017. Risks associated with HSCTs include complications (such as graft-versus-host disease) arising from the use of allogeneic donor stem cells.

With the advent of gene editing technologies, there is now an opportunity to cure SCD patients using autologous stem cells in which the mutation in the β-globin gene responsible for SCD has been corrected. ZFN, TALEN, CRISPR/cas9 and other nuclease-mediated editing approaches could be used to repair, or remove and replace, stem cells from an SCD patient. For example, Sun and Zhao (Biotech. And Bioeng., 2014, 111(5)) demonstrated the successful repair of the human β-globin gene mutation in patient pleuripotent HSCs using TALENs. In addition, Dever, et al., (Nature, 2016, 539:384-389) demonstrated efficient repair of the Glu6Val mutation responsible for SCD in patient HSCs using CRISPR/cas9. Clinical trials using this approach for SCD are now starting.

Unfortunately, standard myeloablative conditioning regimens (i.e., 100% HSC-depleting regimens) using high dose chemotherapy or total body irradiation are currently used for transplants, including for autologous gene-edited cell transplants. There is a need for a safer and more effective conditioning method for these patients. Radiolabeled BC8 (e.g., $^{131}$I-BC8, $^{125}$I-BC8, $^{123}$I-BC8, $^{90}$Y-BC8, $^{177}$Lu-BC8, $^{186}$Re-BC8, $^{188}$Re-BC8, $^{89}$Sr-BC8, $^{153}$Sm-BC8, $^{32}$P-BC8, $^{225}$Ac-BC8, $^{213}$Bi-BC8, $^{213}$Po-BC8, $^{211}$At-BC8, $^{212}$Bi-BC8, $^{213}$Bi-BC8, $^{223}$Ra-BC8, $^{227}$Th-BC8, $^{149}$Tb-BC8, $^{137}$Cs-BC8, $^{212}$Pb-BC8 and $^{103}$Pd-BC8) would be more sparing of a patient's normal tissues. Notably, older patients with SCD may already have organ damage as a result of their disease, and exposure to non-specific radiation or chemotherapy as a myeloablative conditioning regimen could make performing a stem cell transplant even riskier. A radiolabeled BC8 approach presents a better option for these patients.

Further, due to the hereditary nature of the disease, correcting the disease through transplantation of gene-edited HSCs is preferred as early in life as possible, as complications of the disease may be irreversible and have a negative impact on long-term survival for the patient. As such, treating infants or young children afflicted with SCD using gene-edited HSCs is envisioned. To this end, radiolabeled BC8, particularly BC8 labeled with an alpha-emitting radionuclide such as $^{225}$Ac, would be ideal. The use of an alpha-emitting radionuclide such as $^{225}$Ac, with its very short, high energy radiation path length, would focus the radiation on CD45-positive cells and allow for effective myeloablation without the need to isolate treated patients (as would be required for conditioning with a myeloablative dose of a $^{131}$I-BC8).

Example 4—SCID

This example describes HSC ablation preceding transplantation with gene-edited HSCs in patients with SCID.

SCID is a germline genetic disorder in which afflicted patients present with severe T cell defects, with or without accompanying B cell defects. SCID involves a defective adaptive immune response that prevents patients from mounting an effective antibody response to pathogens. SCID is the most severe form of primary immunodeficiencies, and there are at least nine different known genes where mutations lead to SCID. Because SCID patients are incapable of mounting an adaptive immune response, they are susceptible to infection, and early mortality is high. SCID is also known as the "bubble boy" disease because patients must be kept in a sterile environment to avoid life-threatening infections.

The most frequent genetic defect in SCID is in the common gamma chain (γc), which is a protein that is shared by the receptors for interleukins IL-2, IL-4, IL-7, IL-9, IL-15 and IL-21. Other mutated genes that can lead to SCID are ADA and JAK3. As with SCD, only treatment with a stem cell transplant is potentially curative for SCID. However, delayed immune recovery and GVHD are significant risks for these patients. Also, as with SCD patients, SCID patients are young and therefore need effective and safe methods for treatment, including a better conditioning regimen prior to transplant.

Gene editing technology may precisely repair the defect in a SCID patient's own HSCs. Once returned to the body, these engineered HSCs can produce normal lymphocytes and establish a working adaptive immune response to protect against infection. Recently, Chang et al (Cell Reports, 2015, 12:1668-1677) reported effectively restoring normal lymphocyte development via CRISPR/cas9-mediated repair of a mutation in the JAK3 gene in mice. Further Alzubi, et al., (Nature, Scientific Reports, 2017, 7:12475) recently demonstrated using TALEN technology to precisely repair in mice a genetic defect in the IL2RG (common gamma chain), the gene responsible for X-SCID.

It is important that safer and more effective methods for conditioning human SCID patients are developed. Alphaemitter CD45 radioimmunotherapy, such as with $^{225}$Ac-BC8, is needed to safely condition these predominantly young patients.

Example 5—Treatment Synopsis

Table I summarizes selected treatment regimens using gene-edited stem cell administration preceded by HSC depletion via administration of a radiolabeled BC8 antibody (i.e., conditioning agent).

TABLE 1

| Disease | Therapy | Conditioning Agent | Dose |
|---------|---------|---------------------|------|
| SCD | Gene-edited HSCs or Pleuripotent Stem Cells (PSCs) [genes repaired include b-globin (HBB)] | $^{131}$I-BC8 | 200-1,200 mCi [e.g., 200-400 mCi, or 400-1,200 mCi] |
| | | $^{225}$Ac-BC8 | 0.1-5 μCi/kg [e.g., 0.1-1 μCi/kg, 1-3 μCi/kg, or 3-5 μCi/kg] |
| SCID | Gene-edited HSCs or PSCs [genes repaired include JAK3, Janus Family Kinase, ADA, adenosine deaminase, IL2RG, common gamma chain gene] | $^{131}$I-BC8 | 200-1,200 mCi [e.g., 200-400 mCi, or 400-1,200 mCi] |
| | | $^{225}$Ac-BC8 | 0.1-5 μCi/kg [e.g., 0.1-1 μCi/kg, 1-3 μCi/kg, or 3-5 μCi/kg] |
| β-Thalassemia | Gene-edited HSCs or PSCs [genes repaired include b-globin (HBB). BCL11A] | $^{131}$I-BC8 | 200-1,200 mCi [e.g., 200-400 mCi, or 400-1.200 mCi] |
| | | $^{225}$Ac-BC8 | 0.1-5 μCi/kg [e.g., 0.1-1 μCi/kg, 1-3 μCi/kg. or 3-5 μCi/kg] |
| Fanconi's Anemia | Gene-edited HSCs or PSCs [genes repaired include FANCC] | $^{131}$I-BC8 | 200-1,200 mCi [e.g., 200-400 mCi, or 400-1,200 mCi] |
| | | $^{225}$Ac-BC8 | 0.1-5 μCi/kg [e.g., 0.1-1 μCi/kg, 1-3 μCi/kg, or 3-5 μCi/kg] |
| Wiskott-Aldrich Syndrome | Gene-edited HSCs or PSCs [genes repaired include WAS] | $^{131}$I-BC8 | 200-1,200 mCi [e.g., 200-400 mCi, or 400-1,200 mCi] |
| | | $^{225}$Ac-BC8 | 0.1-5 μCi/kg [e.g., 0.1-1 μCi/kg, 1-3 μCi/kg, or 3-5 μCi/kg] |
| AIDS | Gene-edited HSCs or PSCs [genes repaired include CCR5 and CXCR4] | $^{131}$I-BC8 | 200-1,200 mCi [e.g., 200-400 mCi, or 400-1,200 mCi] |
| | | $^{225}$Ac-BC8 | 0.1-5 μCi/kg [e.g., 0.1-1 μCi/kg, 1-3 μCi/kg, or 3-5 μCi/kg] |

What is claimed is:

1. A method for depleting a human subject's hematopoietic stem cells in preparation for administration of a genetically edited hematopoietic stem cell therapy, the method consisting essentially of administering to the subject an effective amount of a radiolabeled anti-CD45 antibody, wherein the radiolabeled anti-CD45 antibody is radiolabeled BC8 comprising $^{131}$I or $^{225}$Ac,
    wherein the subject is afflicted with a non-cancerous disorder treatable via genetically edited hematopoietic stem cell therapy,
    wherein the non-cancerous disorder is selected from the group consisting of a hemoglobinopathy, a congenital immunodeficiency, and a viral infection,
    wherein depleting the subject's hematopoietic stem cells consists of reducing a population of hematopoietic stem cells in the subject by at least 10%, 20%, 30%, 40%, 50%, 60%, 70%, 80%, 90%, 95% or 99%, and wherein
    (i) the radiolabeled BC8 is $^{131}$I-BC8, and the effective amount of $^{131}$I-BC8 is from 10 mCi to 1,200 mCi, or
    (ii) the radiolabeled BC8 is $^{225}$Ac-BC8, and the effective amount of 225Ac-BC8 is selected from the group consisting of from 0.1 μCi/kg to 5.0 μCi/kg subject weight, from 0.1 μCi/kg to 1.0 μCi/kg subject weight, from 1.0 μCi/kg to 3.0 μCi/kg subject weight, and from 3.0 μCi/kg to 5.0 μCi/kg subject weight.

2. The method of claim 1, wherein the effective amount of the radiolabeled BC8 is administered as a single dose.

3. The method of claim 1, wherein the non-cancerous disorder is selected from the group consisting of sickle cell disease (SCD), severe combined immunodeficiency disease (SCID), 0-thalassemia and Fanconi's anemia.

4. The method of claim 3, wherein the non-cancerous disorder is SCD and the genetically edited hematopoietic stem cell therapy is genetically edited β-globin hematopoietic stem cell therapy.

5. The method of claim 3, wherein the non-cancerous disorder is SCID, and wherein an edited gene is selected from the group consisting of the common gamma chain (γc) gene, the adenosine deaminase (ADA) gene and the Janus kinase 3 (JAK3) gene.

6. The method of claim 1, wherein the radiolabeled BC8 is $^{131}$I-BC8, and the effective amount of $^{131}$I-BC8 is from 10 mCi to 200 mCi, from 200 mCi to 400 mCi, or and from 400 mCi to 1,200 mCi.

7. The method of claim 1, wherein the radiolabeled BC8 is $^{225}$Ac-BC8, and the effective amount of $^{225}$Ac-BC8 is selected from the group consisting of from 0.1 μCi/kg to 5.0 μCi/kg subject weight, from 0.1 μCi/kg to 1.0 μCi/kg subject weight, from 1.0 μCi/kg to 3.0 μCi/kg subject weight, and from 3.0 μCi/kg to 5.0 μCi/kg subject weight.

8. A method for treating a human subject afflicted with a non-cancerous disorder treatable via genetically edited hematopoietic stem cell therapy, the method consisting essentially of:
    (i) administering to the subject an effective amount of a radiolabeled anti-CD45 antibody effective to deplete the subject's hematopoietic stem cells, wherein the radiolabeled anti-CD45 antibody is radiolabeled BC8, wherein depleting the subject's hematopoietic stem cells consists of reducing a population of hematopoietic stem cells in the subject by at least 10%, 20%, 30%, 40%, 50%, 60%, 70%, 80%, 90%, 95% or 99%, and
    (ii) after a suitable time period, performing the genetically edited hematopoietic stem cell therapy on the subject to treat the non-cancerous disorder,
    wherein the genetically edited hematopoietic stem cell therapy is allogeneic or autologous stem cell therapy, wherein the non-cancerous disorder is selected from the group consisting of a hemoglobinopathy, a congenital immunodeficiency, and a viral infection, and wherein
(i) the radiolabeled BC8 is $^{131}$I-BC8, and the effective amount of $^{131}$I-BC8 is from 10 mCi to 1,200 mCi, or
(ii) the radiolabeled BC8 is $^{225}$Ac-BC8, and the effective amount of $^{225}$Ac-BC8 is selected from the group consisting of from 0.1 µCi/kg to 5.0 µCi/kg subject weight, from 0.1 µCi/kg to 1.0 µCi/kg subject weight, from 1.0 µCi/kg to 3.0 µCi/kg subject weight, and from 3.0 µCi/kg to 5.0 µCi/kg subject weight.

9. The method of claim 8, wherein the effective amount of the radiolabeled BC8 is administered as a single dose.

10. The method of claim 8, wherein the non-cancerous disorder is selected from the group consisting of sickle cell disease (SCD), severe combined immunodeficiency disease (SCID), 0-thalassemia and Fanconi's anemia.

11. The method of claim 10, wherein the non-cancerous disorder is SCD and the genetically edited hematopoietic stem cell therapy is genetically edited β-globin hematopoietic stem cell therapy.

12. The method of claim 10, wherein the non-cancerous disorder is SCID, and wherein an edited gene is selected from the group consisting of the common gamma chain (γc) gene, the adenosine deaminase (ADA) gene and the Janus kinase 3 (JAK3) gene.

13. The method of claim 8, wherein the radiolabeled BC8 is $^{131}$I-BC8, and the effective amount of $^{131}$I-BC8 is selected from the group consisting of from 10 mCi to 200 mCi administered 6, 7, or 8 days before performing the genetically edited hematopoietic stem cell therapy on the subject to treat the non-cancerous disorder, from 200 mCi to 400 mCi administered 8, 9, 10, 11, or 12 days before performing the genetically edited hematopoietic stem cell therapy on the subject to treat the non-cancerous disorder, and from 400 mCi to 1,200 mCi of $^{131}$I-BC8 administered 10, 11, 12, 13, or 14 days before performing the genetically edited hematopoietic stem cell therapy on the subject to treat the non-cancerous disorder.

14. The method of claim 8, wherein the radiolabeled BC8 is $^{225}$Ac-BC8, and the effective amount of $^{225}$Ac-BC8 is from 0.1 µCi/kg to 5.0 µCi/kg subject weight administered 6, 7, 8, 9, 10, 11, or 12 days before performing the therapy on the subject to treat the non-cancerous disorder.

15. An article of manufacture consisting essentially of (a) a radiolabeled anti-CD45 antibody, wherein the radiolabeled anti-CD45 antibody is radiolabeled BC8 and (b) a label instructing a user to administer to a human subject an amount of the antibody effective to deplete hematopoietic stem cells of the human subject, wherein depleting the hematopoietic stem cells consists of reducing a population of hematopoietic stem cells in the human subject by at least 10%, 20%, 30%, 40%, 50%, 60%, 70%, 80%, 90%, 95% or 99%, and wherein
(i) the radiolabeled BC8 is $^{131}$I-BC8, and the effective amount of $^{131}$I-BC8 is from 10 mCi to 1,200 mCi, or
(ii) the radiolabeled BC8 is $^{225}$Ac-BC8, and the effective amount of $^{225}$Ac-BC8 is selected from the group consisting of from 0.1 µCi/kg to 5.0 µCi/kg subject weight, from 0.1 µCi/kg to 1.0 µCi/kg subject weight, from 1.0 µCi/kg to 3.0 µCi/kg subject weight, and from 3.0 µCi/kg to 5.0 µCi/kg subject weight.

16. The article of claim 15, wherein the radiolabeled BC8 is $^{131}$I-BC8, and the amount of the antibody effective to deplete the hematopoietic stem cells is selected from the group consisting of from 10 mCi to 200 mCi, from 200 mCi to 400 mCi, and from 400 mCi to 1,200 mCi.

17. The article of claim 15, wherein the radiolabeled BC8 is $^{225}$Ac-BC8, and the amount effective to deplete the hematopoietic stem cells is selected from the group consisting of from 0.1 µCi/kg to 5.0 µCi/kg, from 0.1 µCi/kg to 1.0 µCi/kg subject weight, from 1.0 µCi/kg to 3.0 µCi/kg subject weight, and from 3.0 µCi/kg to 5.0 µCi/kg subject weight.

18. The method of claim 1, wherein the radiolabeled BC8 is $^{131}$I-BC8, and the effective amount of $^{131}$I-BC8 is from 70 mCi to 1,200 mCi.

19. The method of claim 1, wherein the radiolabeled BC8 is $^{131}$I-BC8, and the effective amount of $^{131}$I-BC8 is from 300 mCi to 1,200 mCi.

20. The method of claim 1, wherein the radiolabeled BC8 is $^{131}$I-BC8, and the effective amount of $^{131}$I-BC8 is from 70 mCi to 400 mCi.

21. The method of claim 1, wherein the radiolabeled BC8 is $^{131}$I-BC8, and the effective amount of $^{131}$I-BC8 is from 400 mCi to 800 mCi.

22. The method of claim 1, wherein the radiolabeled BC8 is $^{131}$I-BC8, and the effective amount of $^{131}$I-BC8 is from 800 mCi to 1,200 mCi.

23. The method of claim 1, wherein the radiolabeled BC8 is $^{225}$Ac-BC8, and the effective amount of $^{225}$Ac-BC8 is from 0.1 µCi/kg to 5.0 µCi/kg subject weight.

24. The method of claim 1, wherein the radiolabeled BC8 is $^{225}$Ac-BC8, and the effective amount of $^{225}$Ac-BC8 is from 0.1 µCi/kg to 1.0 µCi/kg subject weight.

25. The method of claim 1, wherein the radiolabeled BC8 is $^{225}$Ac-BC8, and the effective amount of $^{225}$Ac-BC8 is from 1.0 µCi/kg to 3.0 µCi/kg subject weight.

\* \* \* \* \*